United States Patent [19]
Hwu et al.

[11] Patent Number: 5,760,013
[45] Date of Patent: Jun. 2, 1998

[54] THYMIDYLATE ANALOGS AND THE USE THEREOF

[75] Inventors: Jih Ru Hwu; Gholam H. Hakimelahi, both of Taipei; Shwu-Chen Tsay, Hsinchu, all of Taiwan

[73] Assignee: National Science Council, Taipei, Taiwan

[21] Appl. No.: 700,795

[22] Filed: Aug. 21, 1996

[51] Int. Cl.$^6$ ........................................... A61K 31/70
[52] U.S. Cl. .......................... 514/49; 514/50; 514/885; 536/22.1; 536/23.1; 536/25.34; 536/25.6; 536/26.8; 536/28.2; 536/28.54
[58] Field of Search .................. 514/49, 50, 885; 536/25.6, 22.1, 23.1, 25.34, 26.8, 28.2, 28.54

[56] References Cited

U.S. PATENT DOCUMENTS

| | | | |
|---|---|---|---|
| 4,689,407 | 8/1987 | Mor et al. . | |
| 4,786,724 | 11/1988 | Letsinger | 536/25.6 |
| 5,122,517 | 6/1992 | Vince et al. | 514/50 |
| 5,132,414 | 7/1992 | Rosowsky et al. . | |
| 5,393,744 | 2/1995 | Huynh Dinh et al. | 536/28.54 |
| 5,489,677 | 2/1996 | Sanghvi et al. | 536/22.1 |
| 5,508,270 | 4/1996 | Baxter et al. . | |
| 5,519,126 | 5/1996 | Hecht | 536/24.3 |
| 5,571,798 | 11/1996 | Harmenberg et al. | 514/49 |
| 5,618,704 | 4/1997 | Sanghvi et al. | 536/22.1 |
| 5,656,745 | 8/1997 | Bischofberger et al. | 536/25.34 |
| 5,663,312 | 9/1997 | Chaturvedula | 536/25.6 |
| 5,670,489 | 9/1997 | Baxter et al. . | |
| 5,672,697 | 9/1997 | Buhr et al. . | |

OTHER PUBLICATIONS

Christopher McGuigan, et al., "Attempts to Introduce Chemotherapeutic Nucleotides into Cells: Studies on the Anti-HIV Agent FDT", Bioorganic & Medicinal Chemistry Letters, vol. 1, No. 12, pp. 729–732, 1991.

Chris Meier and Tam Huynh-Dinh, "o-Alkyl-5',5'-Dinucleoside-Phosphates as Combined Prodrugs of Antiviral and Antibiotic Compounds", Bioorganic & Medicinal Chemistry Letters, vol. 1, No. 10, pp. 527–530, 1991.

Christopher McGuigan, et al., "Synthesis and anti-HIV activity of some haloalkyl phosphoramidate derivatives of 3'-azido-3'-deoxythymidine (AZT) : potent activity of the trichloroethyl methoxyalaninyl compound", Antiviral Research, 15 (1991) 255–263.

Ming S. Chen, eta 1., "Metabolism of 4'-Azidothymidine", The Journal of Biological Chemistry, vol. 267, No. 1, pp. 257–260, Jan. 1992.

Hans Maag, et al., "Synthesis and Anti-HIV Activity of 4'-Azido-and 4'-Methoxynucleosides", J. Med. Chem. 1992, 35, 1440–1451.

G.A. Freeman, et al., "3'-Azido-3',5'-dideoxythymidine-5'-methylphosphonic Acid Diphosphate: Synthesis and HIV-1 Reverse Transcriptase Inhibition", J. Med. Chem. 1992, 35, 3192–3196.

Susan M. Daluge, et al., "5-Chloro-2',3'-Dideoxy-3'-Fluorouridine (935U83) , a Selective Anti-Human Immunodeficiency Virus Agent with an Improved Metabolic and Toxicological Profile", Antimicrobial Agents and Chemotherapy, vol. 38, No. 7, pp. 1590–1603, Jul. 1994.

Primary Examiner—James O. Wilson
Attorney, Agent, or Firm—Hitt Chwang & Gaines, PC

[57] ABSTRACT

Novel thymidylate analogs having the following formula are synthesized in the present invention, which are found active against human immunodeficiency virus type 1 (HIV-1):

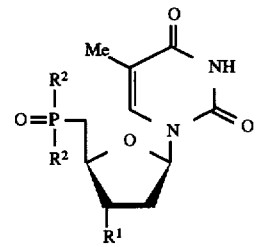

wherein $R^1$ is hydrogen, cyano (—CN), halogen or azido (—$N_3$); $R^2$ is hydroxyl or an amino ester radical having a formula of —$NHR^4COOR^5$, wherein $R^4$ is a bivalent $C_1$–$C_4$ saturated hydrocarbon and $R^5$ is $C_1$–$C_4$ alkyl; Me is methyl; and $R^3$ is hydroxyl or thymidinyl having a formula as follows:

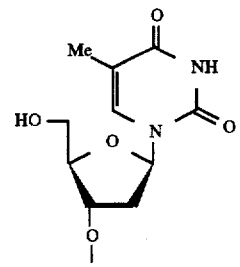

39 Claims, No Drawings

THYMIDYLATE ANALOGS AND THE USE THEREOF

FIELD OF THE INVENTION

The present invention is related generally to synthesis of novel thymidylate analogs and their pharmaceutical use, and more particularly to synthesis of novel thymidylate analogs which are active against human immunodeficiency viruses (HIV).

BACKGROUND OF THE INVENTION

3'-Azido-3'-deoxythymidine (AZT) [Furman, P. A. et al. Proc. Natl. Acad. Sci. U.S.A. 1986, 83, 8333] exhibits remarkable activities against human immunodeficiency virus type 1 (HIV-1). Viral inhibition resulting from AZT appears to require a selective phosphorylation of the compound to give the corresponding monophosphate by thymidine kinase. Then host cell kinases convert the monophosphate to triphosphate. The triphosphate anabolite of AZT is an alternate substrate for HIV-1 reverse transcriptase, which terminates DNA synthesis after incorporation into the growing DNA strand [Reardon, J. E. Biochemistry 1992, 31, 4473; Reardon, J. E. et al. J Biol. Chem. 1990, 265, 20302]. However, the triphosphate intermediate of AZT also affects the activities of the host cell enzymes other than the host cell kinases, which results in the formation of toxic viceproducts. For example, the triphosphate intermediate of AZT is recognized as an alternate substrate by DNA polymerase for syntheses of DNA. Therefore, AZT has a shortcoming in term of its high cellular toxicity.

SUMMARY OF THE INVENTION

The present invention discloses a novel thymidylate analog having the following formula:

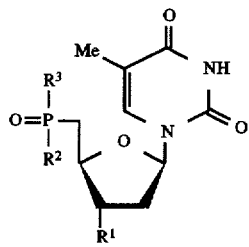

(I)

wherein $R^1$ is hydrogen, cyano (—CN), halogen or azido (—$N_3$);

$R^2$ is hydroxyl or an amino ester radical having a formula of —$NHR^4COOR^5$, wherein $R^4$ is a bivalent $C_1$–$C_4$ saturated hydrocarbon and $R^5$ is $C_1$–$C_4$ alkyl;

Me is methyl; and $R^3$ is hydroxyl or thymidinyl having a formula as follows:

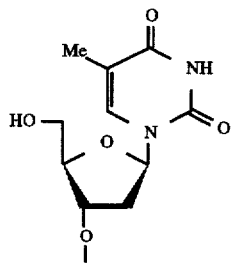

wherein Me is defined as above, or pharmaceutically acceptable salts thereof.

Preferably, $R^2$ of the thymidylate analog of formula (I) is methyl L-alaninate [(L)—$NHCHCH_3CO_2CH_3$] or methyl D-alaninate [(D)—$NHCHCH_3CO_2CH_3$].

Preferably, $R^3$ of the thymidylate analog of formula (I) is the thymidinyl defined as above.

The present invention also provides a pharmaceutical composition for the treatment of a human infected by a human immunodeficiency virus comprising a therapeutically effective amount of the thymidylate analog of the formula (I) or a pharmaceutically acceptable salt thereof, as an active ingredient, in admixture with a pharmaceutically acceptable carrier or diluent for the active ingredient.

The present invention further provides a method for the treatment of a human infected by a human immunodeficiency virus compromising administering a therapeutically effective amount of the thymidylate analog of the formula (I) to a human infected by a human immunodeficiency virus.

The thymidylate analog of formula (I) synthesized in accordance with the present invention has 3'-dehydroxy substituent on its furan ring, and it is believed that the compound of formula (I) can be converted to a monophosphate by thymidine kinase in vivo. The monophosphate is then converted to the triphosphate intermediate by the host cell kinases, which acts as an alternate substrate for HIV reverse transcriptase, and thus terminates viral DNA synthesis after incorporation into the growing DNA strand. This anti-HIV mechanism is similar to that of AZT. Furthermore, the thymidylate analog of formula (I) may has a superior lipophilicity, when $R^2$ is the amino ester radical, which enhances the efficiency of the transport of the thymidylate analog through the cell membranes and thus increases its anti-HIV activity.

In the preferred embodiments of the present invention, the following compounds (III) to (XII) were synthesized. The compounds (III) to (VI) are nucleotide analogs, and the compounds (VII) to (XII) are dinucleotide analogs. Among them Compounds (IX) to (XII) have an amino ester moiety.

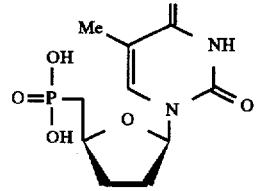

(III)

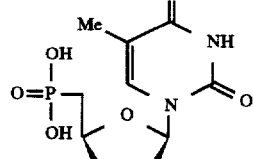

(IV)

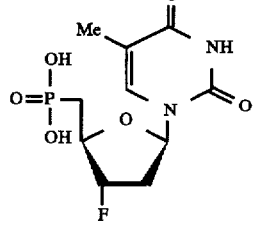

(V)

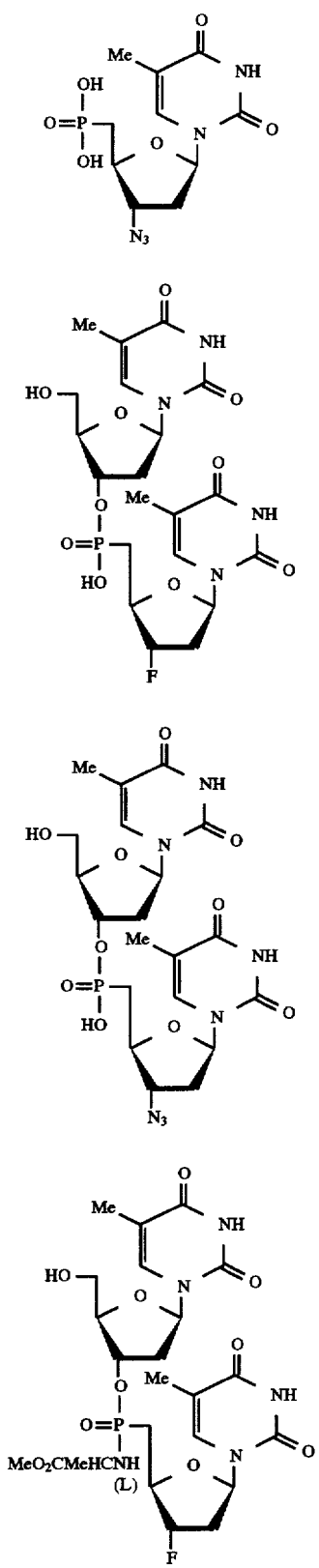
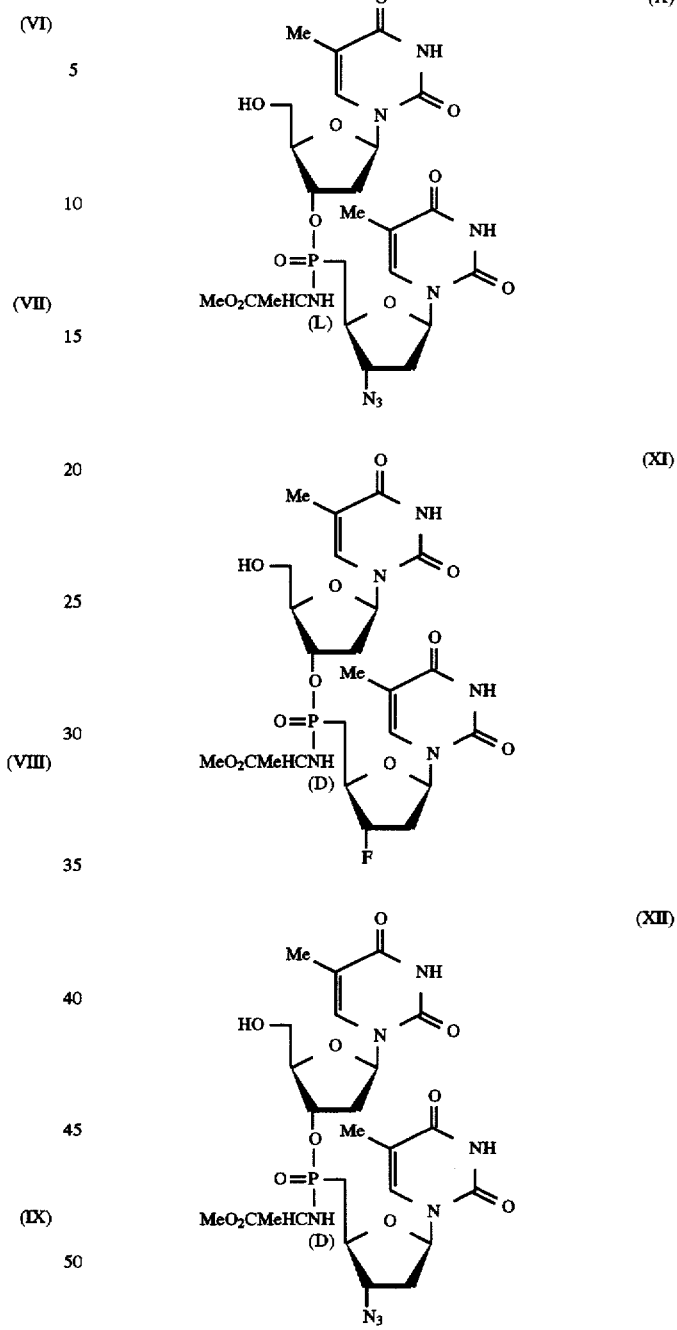
wherein Me is methyl (this definition also applies in the following text).
The invention will be further illustrated by the following examples which are only meant to illustrate the invention, but not to limit it. The reaction routes for synthesizing the title compounds of the Preparation Examples 1–5, 6–12 and 13–22 are shown in the Schemes 1, 2 and 3, respectively.

Scheme 1
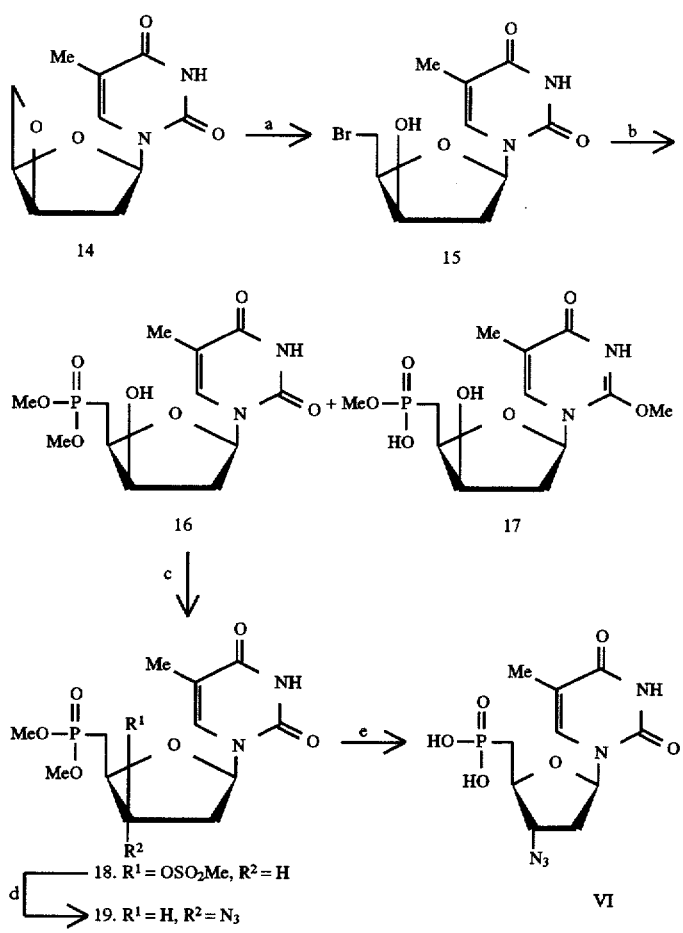
Reagents: (a) LiBr, BF$_3$·OEt$_2$, THF; (b) (MeO)$_3$P, Δ; (c) MeSO$_2$Cl, 4-(dimethylamino)pyridine, pyridine; (d) LiN$_3$, DMF; (e) Me$_3$SiBr, CH$_2$Cl$_2$.
Scheme 2
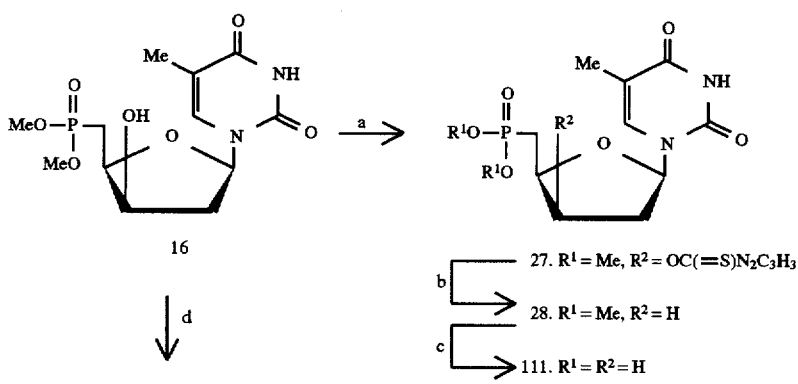

-continued
Scheme 2
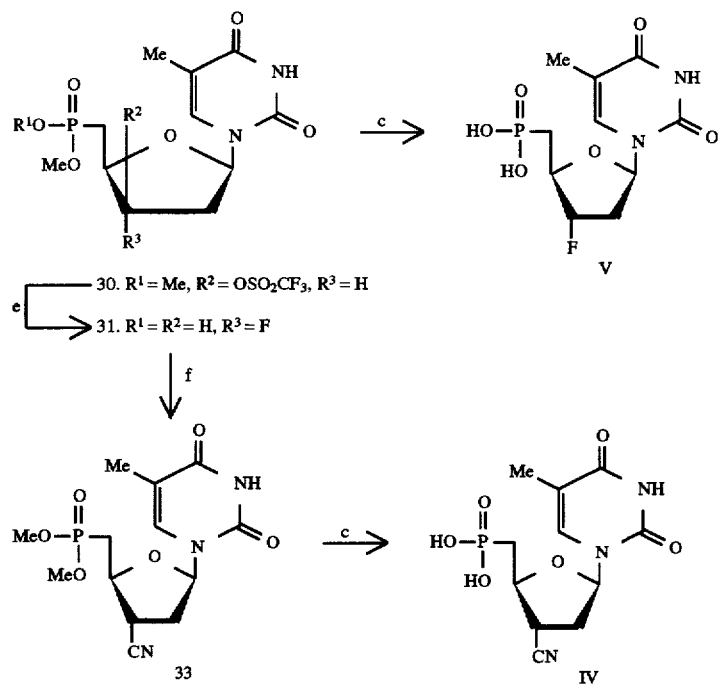
Reagents: (a) (thiocarbonyl)diimidazole, DMF; (b) (n-BU)₃SnH, 2,2'-azobis(2-methylpropionitrile), toluene, Δ; (c) Me₃SiBr, CH₂Cl₂; (d) CF₃SO₂Cl, pyridine; (e) (n-Bu)₄NF, THF; (f) (n-Bu)₄NCN, CH₃CN.
Scheme 3
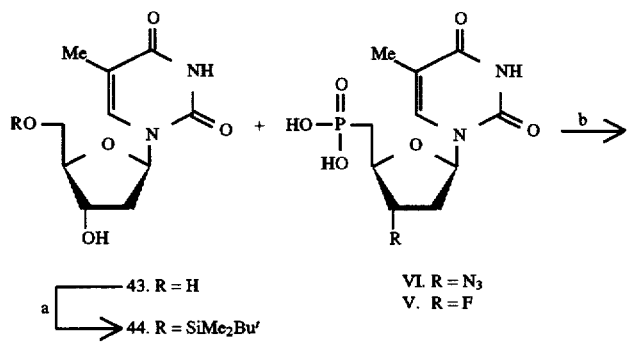

-continued
Scheme 3
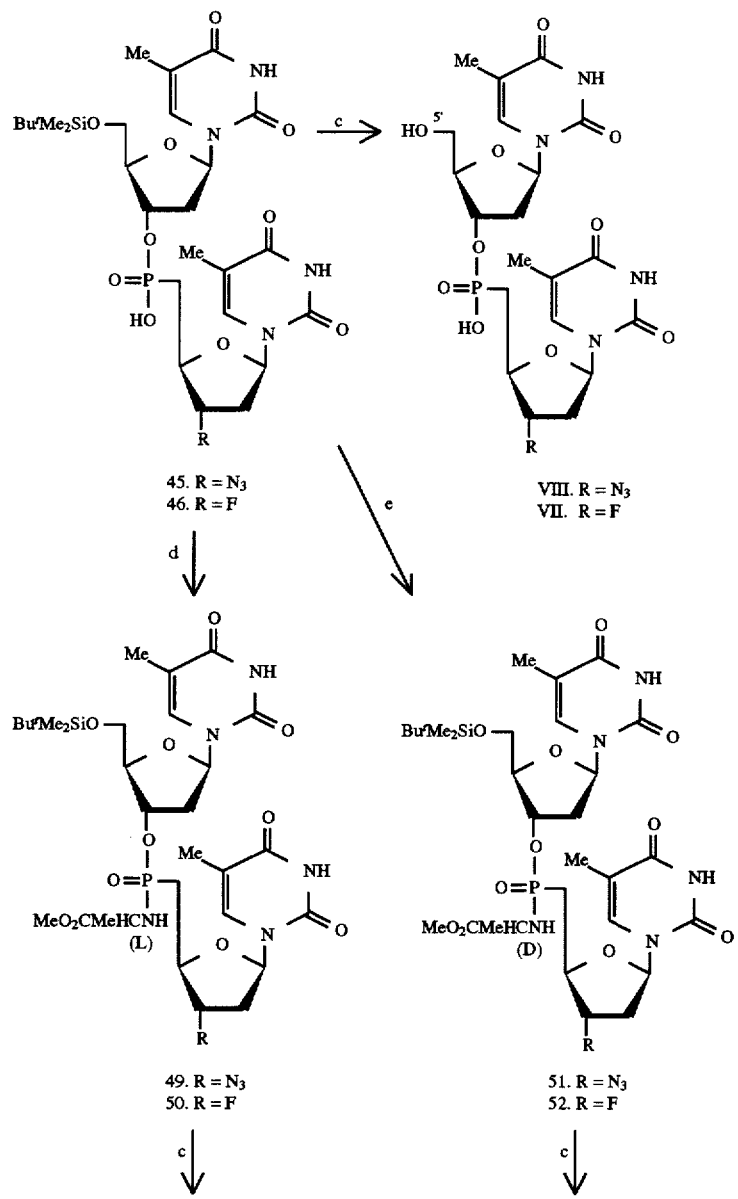

-continued
Scheme 3

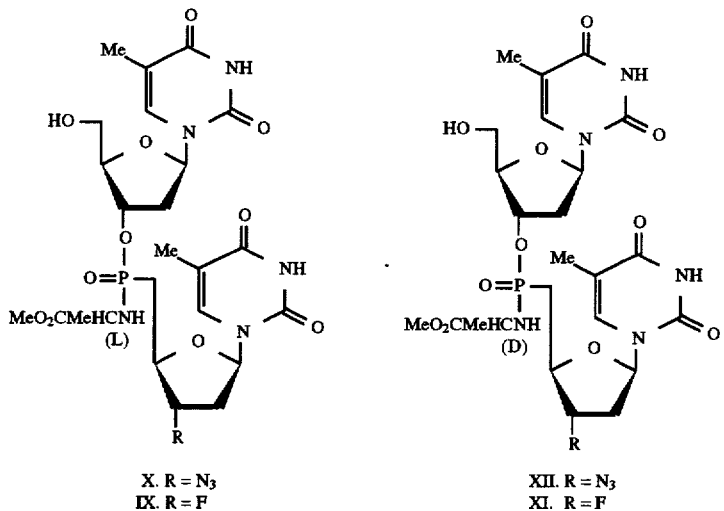

X. R = N₃
IX. R = F

XII. R = N₃
XI. R = F

Reagents: (a) (t-Bu)Me₂SiCl, AgNO₃, THF; (b) CCl₃SO₂Cl, collidine, THF; (c) (n-Bu)₄NF, THF; (d) 2,4,6-(triisopropyl)benzenesulfonyl chloride, methyl L-alaninate, pyridine; (e) 2,4,6-(triisopropyl)benzenesulfonyl chloride, methyl D-alaninate, pyridine.

Preparation Example 1:
1-(5'-Deoxy-5'-bromo-β-D-threo-pentofuranosyl) thymine (15)

To a mixture of BF₃·OEt₂ (OEt₂ and Et₂O both represent ethyl ether) (3.20 mL, 25.0 mmol) and LiBr (2.20 g, 25.0 mmol) in THF (45 mL) was added dropwise a THF solution (10 mL) of 14 (1.12 g, 5.00 mmol) under dry argon at −50° C. The reaction mixture was stirred for 2 h and quenched with saturated NaHCO₃ (15 mL). The solvents were evaporated and the residue was purified by use of column chromatography (SiO₂, AcOEt) (AcOEt represents ethyl acetate) to give 15 (1.01 g) as a foam in 70% yield: TLC Rƒ 0.75 (Et₂O/MeOH=9:1); UV λ$_{max}$ (EtOH): 265 nm (ε 9650); ¹H NMR (CDCl₃/D₂O): δ 1.89 (s, 3 H, CH₃), 2.32 (m, 2 H, H₂C(2')), 3.37 (dd, J=3.0, 6.0 Hz, 2 H, H₂C(5')), 4.10 (m, 1 H, HC(4')), 4.33 (m, 1 H, HC(3')), 5.89 (dd, J=3.3, 7.3 Hz, 1 H, HC(1')), 7.32 (s, 1 H, HC(6)). Anal. (C₁₀H₁₃N₂O₄Br) C, H, N, Br.

Preparation Example 2:
1-[5'-Deoxy-5'-(dimethylphosphono)-β-D-threo-pentofuranosyl]thymine (16) and 1,4-Dihydro-2-methoxy-1-[2',5'-dideoxy-5'-(methylphosphono)-β-D-threo-pentofuranosyl]-4-oxo-5-methylpyrimidine (17)

A mixture of 15 (3.05 g, 10.0 mmol) and trimethyl phosphite (24.8 g, 0.200 mol) was heated at 140° C. The reaction mixture was stirred for 20 h, cooled, and added MeOH (10 mL). The resultant solution was poured into a stirred solution of Et₂O (300 mL) to afford a precipitate. The crude material was purified by use of column chromatography (SiO₂, AcOEt and then AcOEt/acetone=1:1) to afford 16 (1.30 g, 40% yield) and 17 (1.31 g, 40% yield), respectively.

16: mp 150°–152° C.; TLC Rƒ 0.68 (Et₂O/MeOH=9:1); UV λ$_{max}$ (EtOH): 264 nm (ε 9170); ¹H NMR (CDCl₃): δ 1.92 (s, 3 H, CH₃), 2.01–2.65 (m, 4 H, H₂C(2')+H₂C(5')), 3.85 (d, J=11 Hz, 6 H, 2×CH₃O), 4.45 (br m, 2 H, HC(4')+HC(3')), 4.91 (br, 1 H, HOC(3')), 5.71 (dd, J=3.1, 6.9 Hz, 1 H, HC(1')), 7.35 (s, 1 H, HC(6)), 10.20 (br, 1 H, NH). Anal. (C₁₂H₁₉N₂O₇P) C, H, N.

17: mp 199°–201° C.; TLC Rƒ 0.31 (Et₂O/MeOH=9:1); UV λ$_{max}$ (EtOH): 252 nm (ε 7080); ¹H NMR (CDCl₃/DMSO-d₆/D₂O): δ 1.91 (s, 3 H, CH₃), 1.90–2.60 (m, 4 H, H₂C(2')+H₂C(5')), 3.30 (s, 3 H, CH₃O), 3.60 (d, J=11 Hz, 3 H, CH₃OP), 4.44 (m, 2 H, HC(4')+HC(3')), 5.62 (dd, J=3.0, 6.0 Hz, 1 H, HC(1')), 7.40 (s, 1 H, HC(6)). Anal. (C₁₂H₁₉N₂O₇P) C, H, N.

Preparation Example 3:
1-[5'-Deoxy-5'-(dimethylphosphono)-3'-O-mesyl-β-D-threo-pentofuranosyl]thymine (18)

To a pyridine (30 mL) solution containing compound 16 (3.34 g, 10.0 mmol) and 4-dimethylaminopyridine (0.10 g, 0.82 mmol) was added CH₃SO₂Cl (1.20 g, 10.0 mmol) dropwise at 20° C. The mixture was stirred for 24 h and partitioned between AcOEt and H₂O. The organic layer was washed with 5% aqueous HCl solution (3×50 mL), H₂O (50 mL), dried (MgSO₄), filtered, and condensed to give a syrup. The crude material was purified by use of column chromatography (SiO₂, AcOEt) to give 18 (3.70 g) as a foam in 90% yield: TLC Rƒ 0.71 (Et₂O/MeOH=9:1); UV λ$_{max}$ (EtOH): 265 nm (ε 9780); ¹H NMR (CDCl₃): δ 1.90 (s, 3 H, CH₃), 2.00–2.75 (m, 4 H, H₂C(2')+H₂C(5')), 3.15 (s, 3 H, CH₃SO₃), 3.75 (d, J=11 Hz, 6 H, 2×CH₃O), 4.51 (m, 1 H, HC(4')), 5.12 (m, 1 H, HC(3')), 6.08 (dd, J=2.8, 7.8 Hz, 1 H, HC(1')), 7.31 (s, 1 H, HC(6)), 9.50 (br, 1 H, NH). Anal. (C₁₃H₂₁N₂O₉PS) C, H, N.

Preparation Example 4:
1-[3',5'-Dideoxy-3'-azido-5'-(dimethylphosphono)-β-D-erythro-pentofuranosyl]thymine (19)

Compound 18 (2.06 g, 5.00 mmol) and LiN₃ (0.500 g, 10.0 mmol) were dissolved in dry DMF (20 mL) under N₂. The mixture was heated at 95° C. for 4 h; then it was partitioned between AcOEt (50 mL) and H₂O (60 mL). The organic layer was washed with H₂O (3×50 mL), dried (MgSO₄), filtered, and condensed. The residue was purified by use of column chromatography (SiO₂, CHCl₃/AcOEt=1:1) to afford 19 (1.40 g) as a foam in 80% yield: TLC Rƒ 0.27 (Et₂O); UV λ$_{max}$ (EtOH): 264 nm (ε 10100); IR (CH₂Cl₂): 3410 (NH), 2100 (N₃), 1695 cm⁻¹ (2 C=O); ¹H NMR (CDCl₃): δ 1.95 (s, 3 H, CH₃), 2.05–2.50 (m, 4 H, H₂C(2')+H₂C(5')), 3.80 (d, J=12 Hz, 6 H, 2×CH₃O), 3.82–4.03 (m, 2 H, HC(4')+HC(3')), 6.14 (t, J=6.5 Hz, 1 H, HC(1')), 7.19 (s, 1 H, HC(6)), 9.15 (br, 1 H, NH). Anal. (C₁₂H₁₈N₅O₆P) C, H, N.

Preparation Example 5:
3'-Azido-3',5'-dideoxythymidine-5'-phosphonic Acid (VI)

To a solution of 19 (3.60 g, 10.0 mmol) in $CH_2Cl_2$ (50 mL) was added $Me_3SiBr$ (4.95 g, 30.0 mmol); then the solution was stirred at 25° C. for 7 h. A mixture of MeOH and $H_2O$ (5:1, 50 mL) was added and the solvents were evaporated. The product was purified by use of column chromatography ($SiO_2$, AcOEt/MeOH=4:1) to afford VI (2.60 g) as a foam in 80% yield: TLC $Rf$ 0.20 (AcOEt/MeOH=6:1); UV $\lambda_{max}$ (EtOH): 266 nm ($\epsilon$ 10100); IR (Nujol): 3200–3460 (NH, OH), 2100 ($N_3$), 1690 $cm^{-1}$ (2 C=O); $^1H$ NMR ($D_2O$): $\delta$ 1.75 (s, 3 H, $CH_3$), 1.80 (m, 2 H, $H_2C(5')$), 2.15–2.48 (m, 2 H, $H_2C(2')$), 3.78 (m, 1 H, HC(4')), 4.06 (m, 1 H, HC(3')), 6.01 (t, J=6.2 Hz, 1 H, HC(1')), 7.10 (s, 1 H, HC(6)). Anal. ($C_{10}H_{14}N_5O_6P$) C, H, N.

Preparation Example 6:

1-[5'-Deoxy-5'-(dimethylphosphono)-3'-O-(imidazol-1-ylthiocarbonyl)-$\beta$-D-threo-pentofuranosyl]thymine (27)

To a solution of 16 (3.34 g, 10.0 mmol) in DMF (50 mL) was added (thiocarbonyl)diimidazole (5.34 g, 30.0 mmol). The solution was stirred at 25° C. for 8 h and then partitioned between AcOEt (250 mL) and $H_2O$ (250 mL). The organic layer was separated and washed with $H_2O$ (5×100 mL), dried ($MgSO_4$), and condensed. The crude material was purified by use of column chromatography ($SiO_2$, AcOEt) to afford 27 (1.80 g) as a foam in 40% yield: TLC $Rf$ 0.81 ($Et_2O$/MeOH=9:1); UV $\lambda_{max}$ (EtOH): 264 nm ($\epsilon$ 10100); $^1H$ NMR ($CDCl_3$): $\delta$ 1.92 (s, 3 H, $CH_3$), 1.83–2.61 (m, 4 H, $H_2C(2')$ +$H_2C(5')$), 3.80 (d, J=12 Hz, 6 H, 2×$CH_3O$), 4.52 (m, 1 H, HC(4')), 4.81 (m, 1 H, HC(3')), 6.07 (dd, J=3.4, 7.9 Hz, 1 H, HC(1')), 7.39 (s, 1 H, HC(6)), 7.35, 7.87 (2 br s, 2 H, NCH=CHN), 7.99 (s, 1 H, NCH=N), 9.51 (br, 1 H, NH). Anal. ($C_{16}H_{21}N_4O_7SP$) C, H, N, S.

Preparation Example 7:

1-[3',5'-Dideoxy-5'-(dimethylphosphono)-$\beta$-D-pentofuranosyl]thymine (28)

A mixture of 27 (2.66 g, 6.01 mmol), 2,2'-azobis(2-methylpropionitrile) (0.20 g, 1.2 mmol), and (n-Bu)$_3$SnH (7.86 g, 27.0 mmol) in toluene (100 mL) was heated at reflux for 6 h. Solvent was removed at reduced pressure and the residue was purified by use of column chromatography ($SiO_2$, $CHCl_3$/AcOEt=1:1) to give 28 (0.82 g) as a foam in 43% yield: TLC $Rf$ 0.68 (AcOEt); UV $\lambda_{max}$ (EtOH): 264 nm ($\epsilon$ 11000); $^1H$ NMR ($CDCl_3$): $\delta$ 1.91 (d, J=1.1 Hz, 3 H, $CH_3$), 1.71–2.50 (m, 6 H, $H_2C(2')$+$H_2C(3')$+$H_2C(5')$), 3.79 (d, J=11 Hz, 6 H, 2×$CH_3O$), 4.18 (m, 1 H, HC(4')), 6.15 (t, J=6.4 Hz, 1 H, HC(1')), 7.40 (q, J=1.1 Hz, 1 H, HC(6)), 9.18 (br, 1 H, NH). Anal. ($C_{12}H_{19}N_2O_6P$) C, H, N.

Preparation Example 8:

3',5'-Dideoxythymidine-5'-phosphonic acid (III)

The procedure of Preparation Example 5 was repeated except that compound 28 instead of compound 19 was used in the demethylation reaction. TLC $Rf$ 0.22 (AcOEt/MeOH=6:1); UV $\lambda_{max}$ (EtOH): 265 nm ($\epsilon$10500); $^1H$ NMR ($D_2O$): $\delta$ 1.80 (s, 3 H, $CH_3$), 1.68–2.53 (m, 6 H, $H_2C(2')$+$H_2C(3')$+$H_2C(5')$), 3.75 (m, 1 H, HC(4')), 6.05 (t, J=6.3 Hz, 1 H, HC(1')), 7.15 (s, 1 H, HC(6)). Anal. ($C_{10}H_{15}N_2O_6P$) C, H, N.

Preparation Example 9:

1-[3',5'-Dideoxy-3'-fluoro-5'-(methylphosphono)-$\beta$-D-erythro-pentofuranosyl]thymine (31)

To a solution of 16 (3.34 g, 10.0 mmol) in pyridine (30 mL) was added dropwise $CF_3SO_2Cl$ (2.53 g, 15.0 mmol) at 0° C. and the mixture was stirred at the same temperature for 5 h. The solution was partitioned between AcOEt (150 mL) and $H_2O$ (200 mL). The organic layer was separated, washed with 2% aqueous HCl solution (3×60 mL), $H_2O$ (100 mL), dried ($MgSO_4$), filtered, and condensed to afford the crude triflate 30, which was used without further purification. A solution of the crude 30 in THF (30 mL) was treated with (n-Bu)$_4$NF (1.0M solution in THF, 2.00 mL, 20.0 mmol) at 0° C. The reaction mixture was stirred at 25° C. for 13 h; the solvent was evaporated and the residue was purified by use of column chromatography ($SiO_2$, AcOEt) to give 31 (1.60 g) as a foam in 50% yield: TLC $Rf$ 0.18 (AcOEt); UV $\lambda_{max}$ (EtOH): 265 nm ($\epsilon$ 9540); $^1H$ NMR (DMSO-$d_6$/$D_2O$): $\delta$ 1.87 (d, J=1.1 Hz, 3 H, $CH_3$), 1.82–2.66 (m, 4 H, $H_2C(2')$ +$H_2C(5')$), 3.75 (d, J=11 Hz, 3 H, $CH_3O$), 4.25 (m, $J_{4',5}$=3.3 Hz, $J_{4',F}$=28.08 Hz, 1 H, HC(4')), 5.29 (m, $J_{3',F}$=54.1 Hz, 1 H, HC(3')), 6.29 (dd, J=3.9, 9.0 Hz, 1 H, HC(1')), 7.80 (q, J=1.1 Hz, 1 H, HC(6)). Anal. ($C_{11}H_{16}N_2O_6FP$) C, H, N, F.

Preparation Example 10:

3'-Fluoro-3',5'-dideoxythymidine-5'-phosphonic acid (V)

The procedure of Preparation Example 5 was repeated except that compound 31 instead of compound 19 was used in the demethylation reaction. TLC $Rf$ 0.23 (AcOEt/MeOH=6:1); UV $\lambda_{max}$ (EtOH): 263 nm ($\epsilon$ 8989); $^1H$ NMR ($D_2O$): $\delta$ 1.80 (br s, 3 H, $CH_3$), 1.79–2.68 (m, 4 H, $H_2C(2')$+$H_2C(5')$), 4.09 (m, $J_{4',5}$=3.3 Hz, $J_{4',F}$=27.7 Hz, 1 H, HC(4')), 5.27 (m, $J_{3',F}$=54.2 Hz, 1 H, HC(3')), 6.32 (t, J=7.0 Hz, 1 H, HC(1')), 7.52 (s, 1 H, HC(6)). Anal. ($C_{10}H_{14}N_2O_6FP$) C, H, N, F.

Preparation Example 11:

1-[3',5'-Dideoxy-3'-cyano-5'-(dimethylphosphono)-$\beta$-D-erythro-pentofuranosyl]thymine (33)

Compound 16 (1.67 g, 5.01 mmol) was converted to the crude triflate 30 as described in the Preparation Example 9. To a solution of the crude 30 in dry $CH_3CN$ (20 mL) was added n-Bu$_4$NCN (1.36 g, 5.02 mmol) and the mixture was stirred at 25° C. for 2 h. After the solvent was evaporated, the resultant syrup was dissolved in AcOEt (50 mL) and washed with $H_2O$ (2×70 mL). The organic layer was dried ($MgSO_4$), filtered, and condensed. The crude material was purified by use of column chromatography ($SiO_2$, AcOEt/$CHCl_3$=2:1) to afford 33 (0.78 g) as an oil in 45% yield: TLC $Rf$ 0.50 (AcOEt); UV $\lambda_{max}$ (EtOH): 264 nm ($\epsilon$ 9685); IR ($CH_2Cl_2$): 3410 (NH), 2243 (CN), 1696 $cm^{-1}$ (2 C=O); $^1H$ NMR ($CDCl_3$): $\delta$ 1.83 (br s, 3 H, $CH_3$), 1.79–2.52 (m, 4 H, $H_2C(2')$+$H_2C(5')$), 3.49 (m, 1 H, HC(3')), 3.78 (d, J=11 Hz, 6 H, 2×$CH_3O$), 4.13 (m, 1 H, HC(4')), 6.13 (dd, J=3.6, 8.6 Hz, 1 H, HC(1')), 7.42 (br, 1 H, HC(6)), 10.56 (br s, 1 H, NH). Anal. ($C_{13}H_{18}N_3O_6P$) C, H, N.

Preparation Example 12:

3'-Cyano-3',5'-dideoxythymidine-5'-phosphonic acid (IV)

The procedure of Preparation Example 5 was repeated except that compound 33 instead of compound 19 was used in the demethylation reaction. TLC $Rf$ 0.18 (AcOEt/MeOH=6:1); UV $\lambda_{max}$ (EtOH): 265 nm ($\epsilon$ 10100); IR (Nujol): 3200–3460 (NH, OH), 2245 (CN), 1690 $cm^{-1}$ (2 C=O); $^1H$ NMR (DMSO-$d_6$/$D_2O$): $\delta$ 1.79 (s, 3 H, $CH_3$), 1.77–2.60 (m, 4 H, $H_2C(2')$+$H_2C(5')$), 3.50 (m, 1 H, HC(3')), 3.88 (m, 1 H, HC(4')), 6.12 (t, J=6.5 Hz, 1 H, HC(1')), 7.59 (s, 1 H, HC(6)). Anal. ($C_{11}H_{14}N_3O_6P$) C, H, N.

Preparation Example 13:

5'-O-(tert-Butyldimethylsilyl)thymidine (44)

Compound 44 was obtained from thymidine 43 in 98% yield as reported [Hakimelahi, G. H.; Proba, Z. A.; Ogilvie, K. K. New Catalysts and Procedures for the Dimethoxytritylation and Selective Silylation of Ribonucleosides. *Can. J. Chem.* 1982, 60, 1106–1113. Ogilvie, K. K.; Hakimelahi, G. H. A General Method for Selective Silylation of Primary Hydroxyl Groups in Carbohydrates and Related Compounds. *Carbohydr. Res.* 1983, 115, 234–239]. Reagents involved were 43 (2.42 g, 10.0 mmol), (tert-butyl)dimethylsilyl chloride (1.90 g, 12.6 mmol), and $AgNO_3$ (2.21 g, 13.0 mmol). For 44: mp 126°–128° C.; TLC Rƒ 0.42 (Et₂O); UV λ$_{max}$ (EtOH): 264 nm (ε 10600); ¹H NMR (CDCl₃/D₂O): δ 0.17 (s, 6 H, (CH₃)₂Si), 1.01 (s, 9 H, (CH₃)₃C), 1.90 (s, 3 H, CH₃), 2.36 (dd, J=3.0, 6.0 Hz, 2 H, H₂C(2')), 3.71–4.69 (m, 4 H, HC(3')+HC(4')+H₂C(5')), 6.22 (t, J=3.0 Hz, 1 H, HC(1')), 7.46 (s, 1 H, HC(6)). Anal. (C₁₆H₂₈N₂O₅Si) C, H, N.

Preparation Example 14:

(2R,4S,5R)-1-[4-Azidotetrahydro-5-[[[3'-O-[5'-O-(tert-butyldimethylsilyl)thymidinyl]]phosphinico]methyl]-2-furyl]thymine (45)

Collidine (0.61 g, 5.0 mmol) was added to a solution of THF (2.0 mL) containing VI (0.330 g, 0.996 mmol) at −10° C. To this solution was added CCl₃SO₂Cl (0.22 g, 1.0 mmol) in THF (0.50 mL) dropwise. After 44 (0.356 g, 0.999 mmol) in THF (2.0 mL) was added to the mixture, it was stirred at 25° C. for 10 h. The solvents were removed and the residue was dissolved in AcOEt (20 mL) and washed with H₂O (20 mL). The organic layer was concentrated and the residue was purified by use of preparative TLC with a mixture of CHCl₃ and MeOH (6:1) as the eluant. The band at Rƒ ca. 0.67 was eluted with AcOEt to afford 45 (0.435 g, 0.650 mmol) in 65% yield: mp 113°–114° C.; TLC Rƒ 0.67 (CHCl₃/MeOH=6:1); UV λ$_{max}$ (EtOH): 264 nm (ε 15200); ¹H NMR (CDCl₃/DMSO-d₆/D₂O): δ 0.19 (s, 6 H, (CH₃)₂Si), 1.03 (s, 9 H, (CH₃)₃C), 1.85, 1.91 (2 s, 6 H, 2×CH₃C(5)), 1.86–2.63 (m, 6 H, H₂C(2')+H₂C(3)+CH₂P), 3.83–4.72 (m, 6 H, H₂C(5')+HC(4') +HC(5)+HC(3')+HC(4)), 6.10, 6.30 (2 t, J=6.2 Hz, 2 H, HC(1')+HC(2)), 7.28, 7.42 (2 s, 2 H, 2×HC(6)). ³¹P NMR (DMSO-d₆): δ 29.30. Anal. (C₂₆H₄₀N₇O₁₀PSi) C, H, N.

Preparation Example 15:

(2R,4S,5R)-1-[4-Fluorotetrahydro-5-[[[3'-O-[5'-O-(tert-butyldimethylsilyl)thymidinyl]]phosphinico]methyl]-2-furyl]thymine (46)

Compound 46 (0.453 g, 0.700 mmol) was prepared from compound V (0.31 g, 1.0 mmol) and 44 (0.358 g, 1.00 mmol) in 70% yield according to the procedures for the synthesis of 45 in the Preparation Example 14. For 46: mp 108°–110° C.; TLC Rƒ 0.68 (CHCl₃/MeOH=6:1); UV λ$_{max}$ (EtOH): 264 nm (ε 15500); ¹H NMR (CDCl₃/DMSO-d₆/D₂O): δ 0.17 (s, 6 H, (CH₃)₂Si), 1.01 (s, 9 H, (CH₃)₃C), 1.82, 1.92 (2 s, 6 H, 2×CH₃C(5)), 1.83–2.62 (m, 6 H, H₂C(2')+H₂C(3)+CH₂P), 3.85–4.72 (m, 5 H, H₂C(5')+HC(4')+HC(5)+HC(3')), 5.24 (m, J$_{4,F}$=53.0 Hz, 1 H, HC(4)), 6.12–6.38 (m, 2 H, HC(1')+HC(2)), 7.32, 7.48 (2 s, 2 H, 2×HC(6)); ³¹P NMR (DMSO-d₆): δ 29.30. Anal. (C₂₆H₄₀N₄O₁₀FPSi) C, H, N, F.

Preparation Example 16:

(2R,4S,5R)-1-[4-Azidotetrahydro-5-[(3'-O-thymidinyl-phosphinico)methyl]-2-furyl]thymine (VIII)

To a solution of compound 45 (0.67 g, 1.0 mmol) in THF (6.0 mL) was added n-Bu₄NF (1.0M solution in THF, 0.62 g, 2.4 mmol). Acetic acid (1.00 mL) was added to the mixture after it was stirred at 25° C. for 30 min. The solvents were removed and the residue was purified by use of Whatman 3-mm paper with a mixture of i-PrOH, NH₄OH, and H₂O (9:1:2) as the eluant. The band at ca Rƒ 0.20 was eluted with AcOEt to give VIII (0.50 g, 0.90 mmol) in 90% yield: mp 165°–167° C.; TLC Rƒ 0.20 (CHCl₃/MeOH=6:1); paper chromatography, Rƒ 0.75 (i-PrOH/NH₄OH/H₂O= 9:1:2); UV λ$_{max}$ (EtOH): 263 nm (ε 16000); ¹H NMR (DMSO-d₆/D₂O): δ 1.88, 1.90 (2 s, 6 H, 2×CH₃C(5)), 1.87–2.60 (m, 6 H, H₂C(2')+H₂C(3)+CH₂P), 3.55–4.71 (m, 6 H, H₂C(5')+HC(4')+HC(5)+HC(3')+HC(4)), 6.08–6.26 (br m, 2 H, HC(1')+HC(2)), 7.30, 7.50 (2 s, 2 H, 2×HC(6)); ³¹P NMR (DMSO-d₆): δ 29.28. Anal. (C₂₀H₂₆N₇O₁₀P) C, H, N.

Preparation Example 17:

(2R,4S,5R)-1-[4-Fluorotetrahydro-5-[(3'-O-thymidinyl-phosphinico)methyl]-2-furyl]thymine (VII)

Compound VII (0.51 g, 0.95 mmol) was obtained from 46 (0.65 g, 1.0 mmol) in 95% yield according to the procedures for preparation of VIII in the Preparation Example 16. For VII: mp 159°–161° C.; TLC Rƒ 0.21 (CHCl₃/MeOH=6:1); paper chromatography, Rƒ 0.80 (i-PrOH/NH₄OH/H₂O= 9:1:2); UV λ$_{max}$ (EtOH): 263 nm (ε 15600); ¹H NMR (DMSO-d₆/D₂O): δ 1.85, 1.91 (2 s, 6 H, 2×CH₃C(5)), 1.87–2.64 (m, 6 H, H₂C(2')+H₂C(3)+CH₂P), 3.56–4.70 (m, 5 H, H₂C(5')+HC(4')+HC(5)+HC(3')), 5.27 (m, J$_{4,F}$=50.5 Hz, 1 H, HC(4)), 6.10–6.42 (br m, 2 H, HC(1')+HC(2)), 7.39, 7.57 (2 s, 2 H, 2×HC(6)); ³¹P NMR (DMSO-d₆): δ 29.28. Anal. (C₂₀H₂₆N₄O₁₀FP) C, H, N, F.

Preparation Example 18:

(2R,4S,5R)-1-[4-Azidotetrahydro-5-[[[3'-O-[5'-O-(tert-butyldimethylsilyl)thymidinyl]](methoxy-L-alaninyl) phosphinylidene]-methyl]-2-furyl]thymine (Diastereoisomeric Mixture; 49)

To a solution of 45 (0.67 g, 1.0 mmol) in pyridine (6.0 mL) was added 2,4,6-(triisopropyl)benzenesulfonyl chloride (0.54 g, 1.8 mmol). After the mixture was stirred at 25° C. for 13 h, methyl L-alaninate (0.26 g, 2.5 mmol) in pyridine (2.0 mL) was added and the mixture was stirred at 25° C. for 4 h. The solvent was removed and the residue was dissolved in AcOEt (30 mL). The organic layer was washed with H₂O (2×30 mL), dried, and concentrated. The residue was purified by use of preparative TLC with a mixture of CHCl₃ and MeOH (6:1) as the eluant. The band at Rƒ ca. 0.89 was eluted with a mixture of CHCl₃ and MeOH (6:1) to afford compound 49 (0.72 g, 0.95 mmol) in 95% yield: TLC Rƒ 0.89 (CHCl₃/MeOH=6:1); UV λ$_{max}$ (EtOH): 265 nm (ε 16100); ¹H NMR (CDCl₃/D₂O): δ 0.18 (s, 6 H, (CH₃)₂Si), 1.02 (s, 9 H, (CH₃)₃C), 1.40 (d, J=5.8 Hz, 3 H, CH₃), 1.80, 1.90 (2 s, 6 H, 2×CH₃C(5)), 1.82–2.59 (m, 6 H, H₂C(2')+ H₂C(3)+CH₂P), 3.82–4.71 (m, 10 H, H₂C(5')+CH+CH₃O+ HC(4')+HC(5)+HC(3')+HC(4)), 6.12, 6.25 (2 t, J=6.2 Hz, 2 H, HC(1')+HC(2)), 7.30, 7.46 (2 s, 2 H, 2×HC(6)); ³¹P NMR (DMSO-d₆): δ 38.56, 38.70. Anal. (C₃₀H₄₇N₈O₁₁PSi) C, H, N.

Preparation Example 19:

(2R,4S,5R)-1-[4-Fluorotetrahydro-5-[[[3'-O-[5'-O-(tert-butyldimethylsilyl)thymidinyl]](methoxy-L-alaninyl) phosphinylidene]-methyl]-2-furyl]thymine (Diastereoisomeric Mixture; 50)

Compound 50 (0.66 g, 0.90 mmol) was obtained from 46 (0.65 g, 1.0 mmol) in 90% yield according to the procedure for the synthesis of 49 in the Preparation Example 18. For 50: TLC Rƒ 0.92 (CHCl₃/MeOH=6:1); UV λ$_{max}$ (EtOH): 265 nm (ε 16000); ¹H NMR (CDCl₃/D₂O): δ 0.19 (br s, 6 H, (CH₃)₂Si), 1.02 (s, 9 H, (CH₃)₃C), 1.41 (br d, J=5.7 Hz, 3 H, CH₃), 1.79–1.91 (2 s, 6 H, 2×CH₃C(5)), 1.81–2.60 (m, 6 H, H₂C(2')+H₂C(3)+CH₂P), 3.84–4.73 (m, 9 H, H₂C(5') +CH+CH₃O+HC(4')+HC(5)+HC(3')), 5.23 (m, J$_{4,F}$=54.3 Hz, 1 H, HC(4)), 6.11–6.36 (m, 2 H, HC(1')+HC(2)), 7.40, 7.51 (2 s, 2 H, 2×HC(6)); ³¹P NMR (DMSO-d₆): δ 38.56, 38.70. Anal. (C₃₀H₄₇N₅O₁₁FPSi) C, H, N, F.

Preparation Example 20:

(2R,4S,5R)-1-[4-Azidotetrahydro-5-[[[3'-O-[5'-O-(tert-butyldimethylsilyl)thymidinyl]](methoxy-D-alaninyl) phosphinylidene]-methyl]-2-furyl]thymine (Diastereoisomeric Mixture; 51)

Compound 51 (0.66 g, 0.87 mmol) was prepared from 45 (0.67 g, 1.0 mmol) with methyl D-alaninate (0.26 g, 2.5 mmol) in 87% yield as described for the preparation of 49 in the Preparation Example 18. For 51: TLC Rƒ 0.89

(CHCl₃/MeOH=6:1); UV λ_max (EtOH): 265 nm (ε 16150); ¹H NMR (CDCl₃/D₂O): δ 0.18 (s, 6 H, (CH₃)₂Si), 1.02 (s, 9 H, (CH₃)₃C), 1.41 (d, J=6.0 Hz, 3 H, CH₃), 1.80, 1.91 (2 s, 6 H, 2×CH₃ C(5)), 1.81–2.60 (m, 6 H, H₂C(2')+H₂C(3) +CH₂P), 3.81–4.70 (m, 10 H, H₂C(5')+CH+CH₃O+HC(4') +HC(5')+HC(3')+HC(4)), 6.13, 6.26 (2 t, J=6.0 Hz, 2 H, HC(1')+HC(2)), 7.30, 7.46 (2 s, 2 H, 2×HC(6)); ³¹P NMR (DMSO-d₆): δ 38.50, 38.69. Anal. (C₃₀H₄₇N₅O₁₁PSi) C, H, N.

Preparation Example 21:

(2R,4S,5R)-1-[4-Fluorotetrahydro-5-[[[3'-O-[5'-O-(tert-butyldimethylsilyl)thymidinyl]](methoxy-D-alaninyl) phosphinylidene]-methyl]-2-furyl]thymine (Diastereoisomeric Mixture; 52)

Compound 52 (0.70 g, 0.95 mmol) was prepared from 46 (0.65 g, 1.0 mmol) with methyl D-alaninate (0.26 g, 2.5 mmol) in 95% yield as described for the preparation of 49 in the Preparation Example 18. For 52: TLC Rƒ 0.92 (CHCl₃/MeOH=6:1); UV λ_max (EtOH): 265 nm (ε 16080); ¹H NMR (CDCl₃/D₂O): δ 0.18 (br s, 6 H, (CH₃)₂Si), 1.01 (s, 9 H, (CH₃)₃C), 1.42 (br d, J=5.8 Hz, 3 H, CH₃), 1.78, 1.91 (2 s, 6 H, 2×CH₃ C(5)), 1.81–2.61 (m, 6 H, H₂C(2')+H₂C (3)+CH₂P), 3.85–4.74 (m, 9 H, H₂C(5')+CH+CH₃O+HC(4') +HC(5)+HC(3')), 5.24 (m, J_{4,F}=54.4 Hz, 1 H, HC(4)), 6.12–6.36 (m, 2 H, HC(1')+HC(2)), 7.40, 7.50 (2 s, 2 H, 2×HC(6)); ³¹P NMR (DMSO-d₆): δ 38.54, 38.68. Anal. (C₃₀H₄₇N₅O₁₁FPSi) C, H, N, F.

Preparation Example 22:

(2R,4S,5R)-1-[4-Fluorotetrahydro-5-[[(3'-O-thymidinyl) (methoxy-L-alaninyl)-phosphinylidene]methyl]-2-furyl] thymine (Diastereoisomeric Mixture; IX)

(2R,4S,5R)-1-[4-Azidotetrahydro-5-[[(3'-O-thymidinyl) (methoxy-L-alaninyl)-phosphinylidene]methyl]-2-furyl] thymine (Diastereoisomeric Mixture; X)

(2R,4S,5R)-1-[4-Fluorotetrahydro-5-[[(3'-O-thymidinyl) (methoxy-D-alaninyl)-phosphinylidene]methyl]-2-furyl] thymine (Diastereoisomeric Mixture; XI)

(2R,4S,5R)-1-[4-Azidotetrahydro-5-[[(3'-O-thymidinyl) (methoxy-D-alaninyl)-phosphinylidene]methyl]-2-furyl] thymine (Diastereoisomeric Mixture; XII)

Compounds IX, X, XI and XII were prepared from compounds 50 (0.732 g, 1.00 mmol), 49 (0.75 g, 0.99 mmol), 52 (0.732 g, 1.00 mmol) and 51 (0.80 g, 1.0 mmol) respectively, as described for the synthesis of compound VIII in the Preparation Example 16. The crude material was purified by use of TLC plates and eluted with a mixture of CHCl₃ and MeOH (6:1).

Compound IX (0.52 g, 0.85 mmol) in 85% yield: TLC Rƒ 0.62 (CHCl₃/MeOH=6:1); UV λ_max (EtOH): 264 nm (ε 15000); ¹H NMR (DMSO-d₆/D₂O): δ 1.42 (d, J=5.8 Hz, 3 H, CH₃), 1.80, 1.92 (2 s, 6 H, 2×CH₃C(5)), 1.81–2.63 (m, 6 H, H₂C(2')+H₂C(3)+CH₂P), 3.52–4.69 (m, 9 H, H₂C(5')+ CH+CH₃O+HC(4')+HC(5)+HC(3')), 5.25 (m, J_{4,F}=52.0 Hz, 1 H, HC(4)), 6.12–6.39 (br m, 2 H, HC(1')+HC(2)), 7.35, 7.56 (2 s, 2 H, 2×HC(6)); ³¹P NMR (DMSO-d₆): δ 38.52, 38.69. Anal. (C₂₄H₃₃N₅O₁₁FP) C, H, N, F.

Compound X (0.56 g, 0.88 mmol) in 88% yield: TLC Rƒ 0.59 (CHCl₃/MeOH=6:1); UV λ_max (EtOH): 264 nm (ε 14960); ¹H NMR (DMSO-d₆/D₂O): δ 1.40 (d, J=6.0 Hz, 3 H, CH₃), 1.79, 1.91 (2 s, 6 H, 2×CH₃C(5)), 1.80–2.58 (m, 6 H, H₂C(2')+H₂C(3)+CH₂P), 3.54–4.65 (m, 10 H, H₂C(5')+ CH+CH₃O+HC(4')+HC(5)+HC(3')+HC(4)), 6.03, 6.15 (2 t, J=6.8 Hz, 2 H, HC(1')+HC(2)), 7.25, 7.46 (2 s, 2 H, 2×HC(6)); ³¹P NMR (DMSO-d₆): δ 38.52, 38.69. Anal. (C₂₄H₃₃N₈O₁₁P) C, H, N.

Compound XI (0.55 g, 0.90 mmol) in 90% yield: TLC Rƒ 0.70 (CHCl₃/MeOH=6:1); UV λ_max (EtOH): 264 nm (ε 15050); ¹H NMR (DMSO-d₆/D₂O): δ 1.45 (d, J=5.9 Hz, 3 H, CH₃), 1.81, 1.92 (2 s, 6 H, 2×CH₃C(5)), 1.81–2.60 (m, 6 H, H₂C(2')+H₂C(3)+CH₂P), 3.52–4.67 (m, 9 H, H₂C(5')+ CH+CH₃O+HC(4')+HC(5)+HC(3')), 5.26 (m, J_{4,F}=52.0 Hz, 1 H, HC(4)), 6.12–6.40 (br m, 2 H, HC(1')+HC(2)), 7.31, 7.52 (2 br s, 2 H, 2×HC(6)); ³¹P NMR (DMSO-d₆): δ 38.51, 38.68. Anal. (C₂₄H₃₃N₅O₁₁FP) C, H, N, F.

Compound XII (0.55 g, 0.86 mmol) in 86% yield: TLC Rƒ 0.62 (CHCl₃/MeOH=6:1); UV λ_max (EtOH): 264 nm (ε 15000); ¹H NMR (DMSO-d₆/D₂O): δ 1.47 (d, J=6.0 Hz, 3 H, CH₃), 1.80, 1.91 (2 s, 6 H, 2×CH₃C(5)), 1.80–2.59 (m, 6 H, H₂C(2')+H₂C(3)+CH₂P, 3.55–4.66 (m,10 H, H₂C(5')+ CH+CH₃O+HC(4')+HC(5)+HC(3')+H—C(4)), 6.05, 6.14 (2 t, J=6.8 Hz, 2 H, HC(1')+HC(2)), 7.25, 7.45 (2 br s, 2 H, 2×HC(6)); ³¹P NMR (DMSO-d₆): δ 38.51, 38.68. Anal. (C₂₄H₃₃N₈O₁₁P) C, H, N.

Example 1: Determination of Solubility and Partition Coefficients (Lipophilicity) of Thymidylate Analogs Determination of Solubility. Each compound (70 mg) listed in Table 1 was agitated in a 25-mL volumetric flask with phosphate buffer (0.10M, 5.0 mL) for 20 h. This solution was filtered from undissolved solid through a sintered glass funnel (4.0–5.5 mesh ASTM) and the concentration of the solution was determined by UV absorbance (Table 1).

Determination of Partition Coefficients (Lipophilicity). A solution of each compound (10 mL) in Table 1 in phosphate buffer (0.10M) possessing an UV absorbance of 2.2–3.3 at 258–265 nm was shaken with 1-pentanol (10 mL) in a separatory funnel for 1.5 h. The layers were separated, and their concentrations were determined by an UV spectrophotometer. The partition coefficient was calculated as $P=[S]_{1\text{-}pentanol}/[S]_{H_2O}$ (Table 1).

TABLE 1

Solubility in H₂O and Lipophilicity of Nucleoside and Nucleotide Analogs

| compound | solubility in H₂O (mg/mL) | log P[a] |
|---|---|---|
| AZT | 1.24 | 2.86 |
| V | 12.26 | 0.19 |
| VI | 11.12 | 0.16 |
| VII | 3.98 | 0.28 |
| VIII | 3.24 | 0.27 |
| IX | 8.79 | 2.46 |
| X | 9.13 | 2.38 |
| XI | 8.92 | 2.48 |
| XII | 9.20 | 2.33 |

[a]Partition coefficients were calculated as follows:
$P = [Substrate]_{1\text{-}pentanol}/[Substrate]_{H_2O}$.

It can be seen from Table 1 that phosphonoamidates IX–XII have higher lipophilicity than the corresponding nucleoside phosphonates V and VI as well as the dinucleotide phosphonates VII and VIII, which is comparable to that of AZT. The water solubility of compounds V and XII is higher than that of AZT.

Example 2: Inhibitory Effects of Nucleoside and Nucleotide Analogs on the Cytopathogenicity of HIV-1(III B) in MT4 Cell and Cellular Toxicity We tested the synthesized compounds III–XII as well as AZT for their inhibition of cytopathogenicity of human immunodeficiency virus type 1 (HIV-1)(IIIB) in MT4 cells in a cell-protection assay. Toxicity of these compounds was evaluated by their ability to cause morphological changes in cells at different concentrations. The minimum inhibitory concentrations (IC₅₀), measured by use of the linear regression method, are summarized in Table 2.

We can see from the data shown in Table 2 that the thymidylate analogs III–XII synthesized in accordance with the present invention demonstrate the ability to protect MT4 cells from HIV, which exhibits a cytopathic effect, with the exception of compound IV. Furthermore, the present compounds IX–XII have an antiviral activity against HIV-1 (IIIB) comparable to that of AZT with a significantly lower cellular toxicity.

TABLE 2

Inhibitory Effects of Nucleoside and Nucleotide Analogs Synthesized in Accordance with the Present Invention.

| compound | $IC_{50}$ ($\mu g/mL$)[a] HIV-1(III B) | MT4 cell[b] |
|---|---|---|
| AZT | 0.02 | 57.28 |
| III | 23.50 | 128.43 |
| IV | c | 69.87 |
| V | 11.79 | 98.70 |
| VI | 7.68 | 114.57 |
| VII | 3.04 | 78.97 |
| VIII | 1.92 | 99.53 |
| IX | 0.34 | 180.06 |
| X | 0.61 | 199.78 |
| XI | 0.50 | 462.00 |
| XII | 0.76 | 457.50 |

[a]Inhibitory concentrations ($IC_{50}$) represent the average of triplicate determinations;
[b]Concentration of the compound required to reduce the number of viable uninfected cells by 50%; and
[c]Not active up to 128 $\mu g/mL$.

The embodiments of the present invention described above are to be regarded in all respects as being merely illustrative and not restrictive. Accordingly, the present invention may be embodied in other specific forms without deviating from the spirit thereof. The present invention is therefore to be limited only by the scopes of the following appended claims.

What is claimed is:

1. A thymidylate analog having the following formula:

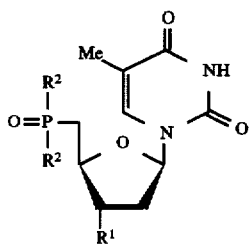

wherein $R^1$ is hydrogen, cyano (—CN), halogen or azido (—$N_3$);

$R^2$ is hydroxyl or an amino ester radical having a formula of —$NHR^4COOR^5$, wherein $R^4$ is a bivalent $C_1$–$C_4$ saturated hydrocarbon and $R^5$ is $C_1$–$C_4$ alkyl;

Me is methyl; and $R^3$ is hydroxyl or thymidinyl having a formula as follows:

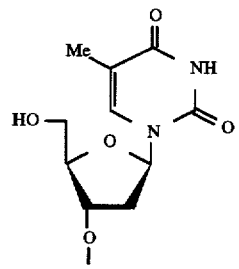

wherein Me is defined as above, or pharmaceutically acceptable salts thereof.

2. The thymidylate analog as defined in claim 1, wherein $R^3$ is thymidinyl having the following formula:

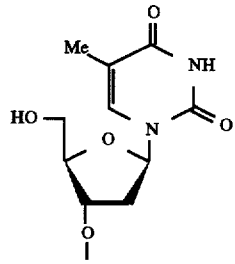

wherein Me is methyl.

3. The thymidylate analog as defined in claim 1, wherein $R^2$ is methyl L-alaninate [(L)—$NHCHCH_3CO_2CH_3$] or methyl D-alaninate [(D)—$NHCHCH_3CO_2CH_3$].

4. The thymidylate analog as defined in claim 2, wherein $R^2$ is methyl L-alaninate [(L)—$NHCHCH_3CO_2CH_3$] or methyl D-alaninate [(D)—$NHCHCH_3CO_2CH_3$].

5. The thymidylate analog as defined in claim 3, wherein $R^2$ is methyl D-alaninate [(D)—$NHCHCH_3CO_2CH_3$].

6. The thymidylate analog as defined in claim 4, wherein $R^2$ is methyl D-alaninate [(D)—$NHCHCH_3CO_2CH_3$].

7. The thymidylate analog as defined in claim 1, wherein $R^1$ is halogen or azido.

8. The thymidylate analog as defined in claim 7, wherein $R^1$ is halogen.

9. The thymidylate analog as defined in claim 8, wherein $R^1$ is —F.

10. The thymidylate analog as defined in claim 2, wherein $R^1$ is halogen or azido.

11. The thymidylate analog as defined in claim 4, wherein $R^1$ is halogen or azido.

12. The thymidylate analog as defined in claim 11, wherein $R^1$ is halogen.

13. The thymidylate analog as defined in claim 12, wherein $R^1$ is —F.

14. A pharmaceutical composition for the treatment of a human infected by a human immunodeficiency virus comprising a therapeutically effective amount of the thymidylate analog as defined in claim 1 or a pharmaceutically acceptable salt thereof, as an active ingredient, in admixture with a pharmaceutically acceptable carrier or diluent for the active ingredient.

15. The pharmaceutical composition as defined in claim 14, wherein $R^3$ is thymidinyl having the following formula:

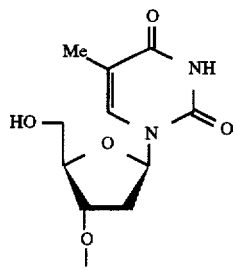

wherein Me is methyl.

16. The pharmaceutical composition as defined in claim 14, wherein $R^2$ is methyl L-alaninate [(L)—NHCHCH$_3$CO$_2$CH$_3$] or methyl D-alaninate [(D)—NHCHCH$_3$CO$_2$CH$_3$].

17. The pharmaceutical composition as defined in claim 15, wherein $R^2$ is methyl L-alaninate [(L)—NHCHCH$_3$CO$_2$CH$_3$] or methyl D-alaninate [(D)—NHCHCH$_3$CO$_2$CH$_3$].

18. The pharmaceutical composition as defined in claim 16, wherein $R^2$ is methyl D-alaninate [(D)—NHCHCH$_3$CO$_2$CH$_3$].

19. The pharmaceutical composition as defined in claim 17, wherein $R^2$ is methyl D-alaninate [(D)—NHCHCH$_3$CO$_2$CH$_3$].

20. The pharmaceutical composition as defined in claim 14, wherein $R^1$ is halogen or azido.

21. The pharmaceutical composition as defined in claim 20, wherein $R^1$ is halogen.

22. The pharmaceutical composition as defined in claim 21, wherein $R^1$ is —F.

23. The pharmaceutical composition as defined in claim 15, wherein $R^1$ is halogen or azido.

24. The pharmaceutical composition as defined in claim 17, wherein $R^1$ is halogen or azido.

25. The pharmaceutical composition as defined in claim 24, wherein $R^1$ is halogen.

26. The thymidylate analog as defined in claim 25, wherein $R^1$ is —F.

27. A method for the treatment of a human infected by a human immunodeficiency virus comprising administering a therapeutically effective amount of the thymidylate analog as defined in claim 1 to a human infected by a human immunodeficiency virus.

28. The method as defined in claim 27, wherein $R^3$ is thymidinyl having the following formula:

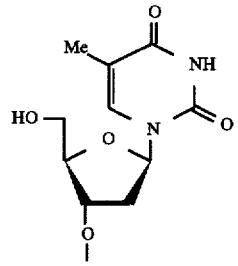

wherein Me is methyl.

29. The method as defined in claim 27, wherein $R^2$ is methyl L-alaninate [(L)—NHCHCH$_3$CO$_2$CH$_3$] or methyl D-alaninate [(D)—NHCHCH$_3$CO$_2$CH$_3$].

30. The method as defined in claim 28, wherein $R^2$ is methyl L-alaninate [(L)—NHCHCH$_3$CO$_2$CH$_3$] or methyl D-alaninate [(D)—NHCHCH$_3$CO$_2$CH$_3$].

31. The method as defined in claim 29, wherein $R^2$ is methyl D-alaninate [(D)—NHCHCH$_3$CO$_2$CH$_3$].

32. The method as defined in claim 30, wherein $R^2$ is methyl D-alaninate [(D)—NHCHCH$_3$CO$_2$CH$_3$].

33. The method as defined in claim 27, wherein $R^1$ is halogen or azido.

34. The method as defined in claim 33, wherein $R^1$ is halogen.

35. The method as defined in claim 34, wherein $R^1$ is —F.

36. The method as defined in claim 28, wherein $R^1$ is halogen or azido.

37. The method as defined in claim 30, wherein $R^1$ is halogen or azido.

38. The method as defined in claim 37, wherein $R^1$ is halogen.

39. The method as defined in claim 38, wherein $R^1$ is —F.

* * * * *